United States Patent [19]
Tomikawa et al.

[11] Patent Number: 4,937,266
[45] Date of Patent: Jun. 26, 1990

[54] INHIBITORY AGENT OF HEPATIC FIBROSIS

[75] Inventors: Munehiro Tomikawa; Junichiro Wakasugi, both of Tokyo, Japan

[73] Assignee: Daiichi Seiyaku Co., Ltd., Tokyo, Japan

[21] Appl. No.: 292,793

[22] Filed: Jan. 3, 1989

[30] Foreign Application Priority Data

Jan. 6, 1988 [JP] Japan ................................ 63-1067

[51] Int. Cl.$^5$ ............................................ A61K 31/16
[52] U.S. Cl. .................................... 514/616; 514/629
[58] Field of Search ................................ 514/629, 616

[56] References Cited
PUBLICATIONS

Cecil Textbook of Medicine, pp. 799–801, (1982).
Miyazawa et al., Chem. Abst., 97:54582n, (1982).

Primary Examiner—Douglas W. Robinson
Assistant Examiner—Zohreh A. Fay
Attorney, Agent, or Firm—Sughrue, Mion, Zinn, Macpeak & Seas

[57] ABSTRACT

An inhibitory agent of hepatic fibrosis containing pantethine as an active ingredient.

1 Claim, No Drawings

INHIBITORY AGENT OF HEPATIC FIBROSIS

FIELD OF THE INVENTION

This invention relates to an inhibitory agent of hepatic fibrosis containing pantethine as an active ingredient.

BACKGROUND OF THE INVENTION

Haptatic fibrosis means an abnormal increase in fibrous connective tissue following hepatic diseases such as alcoholic heptatitis. Heptatic fibrosis induces excessive deposition of connective tissue such as collagen and, at the same time, causes dysfunction of the liver. The progressing of hepatic fibrosis finally causes cirrhosis.

Intensive studies have conventionally been made on agents for preventing or inhibiting hepatic fibrosis but have not yet found an effective agent.

Pantethine (D-bis-(N-pantothenyl-$\beta$-aminoethyl)-disulfide) has been reported to be effective on hepatic diseases such as medicinal fatty liver in JP-B-No. 60-19891 (the term "JP-B" as used herein means an "examined published Japanese patent application) and viral hepatitis in JP-A-No. 58-35118 (the term "JP-A" as used herein means an "unexamined published Japanese patent application"). These effects of pantethine, however, have no connection with the inhibition of hepatic fibrosis.

SUMMARY OF THE INVENTION

As a result of extensive researches, the inventors have found that pantethine inhibited hepatic fibrosis and thus reached the present invention.

This invention relates to an inhibitory agent of hepatic fibrosis containing pantethine as an active ingredient.

DETAILED DESCRIPTION OF THE INVENTION

Pentethine is a compound of high safety, and an acute toxicity ($LD_{50}$) thereof in mice was over 10 g/kg-body weight (p.o.).

Dosage forms of the inhibitory agent of hepatic fibrosis according to the present invention include tablets, powders, granules, capsules, injectable solutions, and the like. These dosage forms can be prepared using conventional pharmaceutical techniques by combining pantethine, the main ingredient, with vehicles (e.g., starch, cellulose), disintegrators, stabilizers, etc.

The agents of the invention are usually administered orally or parenterally at a dose level of from 200 to 2,000 mg/day for an adult (about 60 kg body weight) in oral administration.

The main component of fibrous connective tissue playing an important role in hepatic fibrosis is collagen, and it is known that collagen synthesis is accelerated during the progression of hepatic fibrosis. It is also known that prolyl hydroxylase acts as a rate limiting enzyme in collagen synthesis and the increase in the activity of the enzyme in the liver is closely correlated with the appearance and progression of hepatic fibrosis.

As is demonstrated in example hereinafter given, the agent of the present invention significantly inhibited an increase in prolyl hydroxylase activity in the liver of a hepatic fibrosis model induced by cholesterol-feeding. The agent of the present invention is therefore excellent as an inhibitory agent of hepatic fibrosis.

The present invention is now illustrated in greater detail by the following example, but it should be understood that the present invention is not construed as being limited thereto.

EXAMPLE

Test Animals

Male Japanese white rabbits weighing 2.5 kg were used. A cholesterol group consisting of 8 rabbits were fed on RC-4 diet (sold by Oriental Kobo Co., Ltd.) containing 0.5% cholesterol for 10 weeks. A pantethine group consisting of 9 rabbits were fed on RC-4 diet containing 0.5% cholesterol and 1% pantethine for 10 weeks. A control group consisting of 3 rabbits were fed on RC-4 diet for the same period.

Prolyl Hydroxylase Assay

The rabbits were sacrificed by exsangunation from abdominal aorta under anesthesia with pentobarbital and the liver and kidney were removed. A portion of the each organ was homogenized with 9 times the volume of a 0.01M Tris-hydrochloric acid buffer solution (pH 7.4) containing $10^{-5}M$ EDTA and $10^{-4}M$ DTT in Polytron homogenizer. The prolyl hydroxylase activity was expressed as radioactivity of $^3H_2O$ released per milligram of protein when $^3H$-proline labeled unhydroxylated collagen was incubated as a substrate for 30 minutes. That is, 800 $\mu$l of a substrate mixture having the composition shown in Table 1 below was added to 200 $\mu$l of the homogenate. Incubation was carried out at 30° C. for 30 minutes. 100 $\mu$l of a 55% trichloroacetic acid aqueous solution was added thereto to stop the reaction. The $^3H_2O$ of the reaction mixture was separated by vacuum distillation of the whole reaction mixture. An aliquot (800 $\mu$l) of the distillate was mixed with 10 ml of Aquasol and counted for the radioactivity in a liquid scintillation counter. The protein amount was measured by BIO.RAD Protein Assay Kit using bovine serum albumin (BSA) as a standard.

TABLE 1

| Composition of Substrate Mixture | |
|---|---|
| 0.5 M Tris-HCl buffer solution | 3.1 ml |
| Ascorbic acid (220 mg/250 ml) | 3.1 ml |
| $FeNH_4SO_4$ (198 mg/250 ml) | 3.1 ml |
| 1% BSA | 3.1 ml |
| Catalase (1 g/50 ml) | 3.1 ml |
| $\alpha$-Ketoglutaric acid (36.5 mg/250 ml) | 3.1 ml |
| $^3H$-Proline-labeled collagen solution | 3.1 ml |
| Distilled water | 2.48 ml |

The prolyl hydroxylase activity of the liver and the kidney thus determined are shown in Table 2.

TABLE 2

| Prolyl Hydroxylase Activity in Liver and Kidney | | |
|---|---|---|
| | Prolyl Hydroxylase Activity (cpm/mg-protein)* | |
| Group | Liver | Kidney |
| Normal group | 522.8 ± 45.8 | |
| Cholesterol group | 1349.6 ± 145.0** | 600.9 ± 79.5 |
| Pantethine | 729.3 ± 45.6*** | 672.3 ± 65.8 |

TABLE 2-continued

| Prolyl Hydroxylase Activity in Liver and Kidney | | |
|---|---|---|
| | Prolyl Hydroxylase Activity (cpm/mg-protein)* | |
| Group | Liver | Kidney |
| group | | |

Note:
*mean ± standard error
**P > 0.01 vs. normal group (student t-test)
***P > 0.01 vs. cholesterol group (student t-test)

As is apparent from Table 2, the prolyl hydroxylase activity in the liver of the cholesterol group significantly increased to about 2.6 times the level of the normal group. This stimulation of the activity of proryl hydroxylase indicates that cholesterol-feeding induced an increase in collagen synthesis, and hepatic fibrosis was observed in the cholesterol group. To the contrary, the prolyl hydroxylase activity in the liver of the pantethine group was decreased nearly to the level of the normal group by administering pantethine. Pantethine was thus proved inhibitory on hepatic fibrosis.

On the other hand, pantethine exerted no effect on prolyl hydroxylase in the kidney, suggesting that the inhibitory activity of pantethine on fibrosis is specific to heptic fibrosis.

While the invention has been described in detail and with reference to specific embodiments thereof, it will be apparent to one skilled in the art that various changes and modifications can be made therein without departing from the spirit and scope thereof.

What is claimed is:

1. A method of inhibiting hepatic fibrosis which comprises administering an amount of pantethine effective to inhibit said hepatic fibrosis.

* * * * *